(12) United States Patent
Kienzle et al.

(10) Patent No.: US 6,352,541 B1
(45) Date of Patent: Mar. 5, 2002

(54) MAGAZINE FOR A SURGICAL CLIP APPLICATOR

(75) Inventors: Karl-Ernst Kienzle, Immendingen; Rupert Mayenberger, Rielasingen; Dieter Weisshaupt, Immendingen, all of (DE)

(73) Assignee: Aesculap AG & Co. KG, Tuttlingen (DE)

( * ) Notice: Subject to any disclaimer, the term of this patent is extended or adjusted under 35 U.S.C. 154(b) by 0 days.

(21) Appl. No.: 09/570,459

(22) Filed: May 12, 2000

Related U.S. Application Data

(63) Continuation of application No. PCT/EP98/06775, filed on Oct. 24, 1998.

(30) Foreign Application Priority Data

Nov. 26, 1997 (DE) .......................................... 197 52 331

(51) Int. Cl.7 ............................................... A61B 17/03
(52) U.S. Cl. ...................................... 606/143; 606/157
(58) Field of Search ............................... 606/139, 142, 606/143, 151, 157, 158; 227/901

(56) References Cited

U.S. PATENT DOCUMENTS

| 4,478,220 A | * 10/1984 | DiGiovanni | 606/143 |
| 4,854,317 A | 8/1989 | Braun | 606/143 |
| 4,983,176 A | 1/1991 | Cushman et al. | 606/143 |
| 5,047,038 A | * 9/1991 | Peters et al. | 606/139 |
| 5,207,692 A | 5/1993 | Kraus et al. | 606/143 |
| 5,772,673 A | * 8/1998 | Cuny | 606/142 |

FOREIGN PATENT DOCUMENTS

| DE | 37 04 760 | 3/1988 |
| DE | 690 28 200 | 2/1997 |
| DE | 691 22 002 | 2/1997 |
| WO | WO 96/32891 | 10/1996 |

\* cited by examiner

*Primary Examiner*—Gary Jackson
(74) *Attorney, Agent, or Firm*—Barry R. Lipsitz

(57) ABSTRACT

In order to be able to simplify the construction of a magazine for a surgical clip applicator comprising a receiving chamber for clips which are arranged one behind the other, are displaceable in the receiving chamber towards its open end and have two arms connected via a bridge and pivotable away from one another into an open position contrary to an elastic force and projections associated with these arms and projecting rearwards beyond the bridge, and comprising two opening tools which are located opposite one another, are movable towards one another like pincers and can be abutted on the projections of the respectively foremost clip, it is suggested that the opening tools be connected in a hinge-like manner to an advancing element displaceable in the magazine parallel to the direction of displacement of the clips and during its advancing movement in the direction towards the open end of the receiving chamber come to rest on a deflection surface of the magazine and thereby be pivoted inwards transversely to the direction of displacement towards the opening tool located respectively opposite.

21 Claims, 4 Drawing Sheets

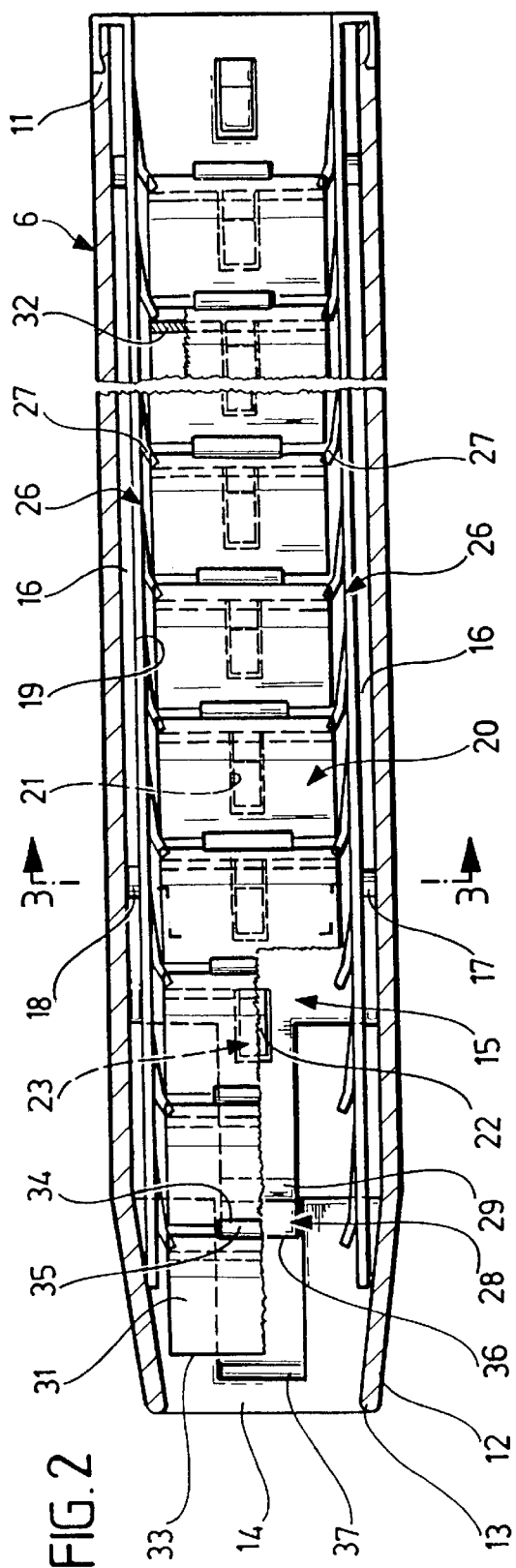
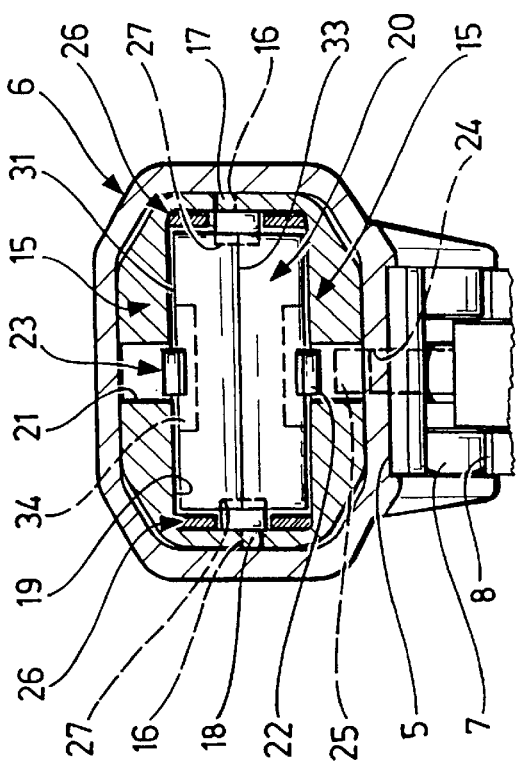
FIG. 2
FIG. 3

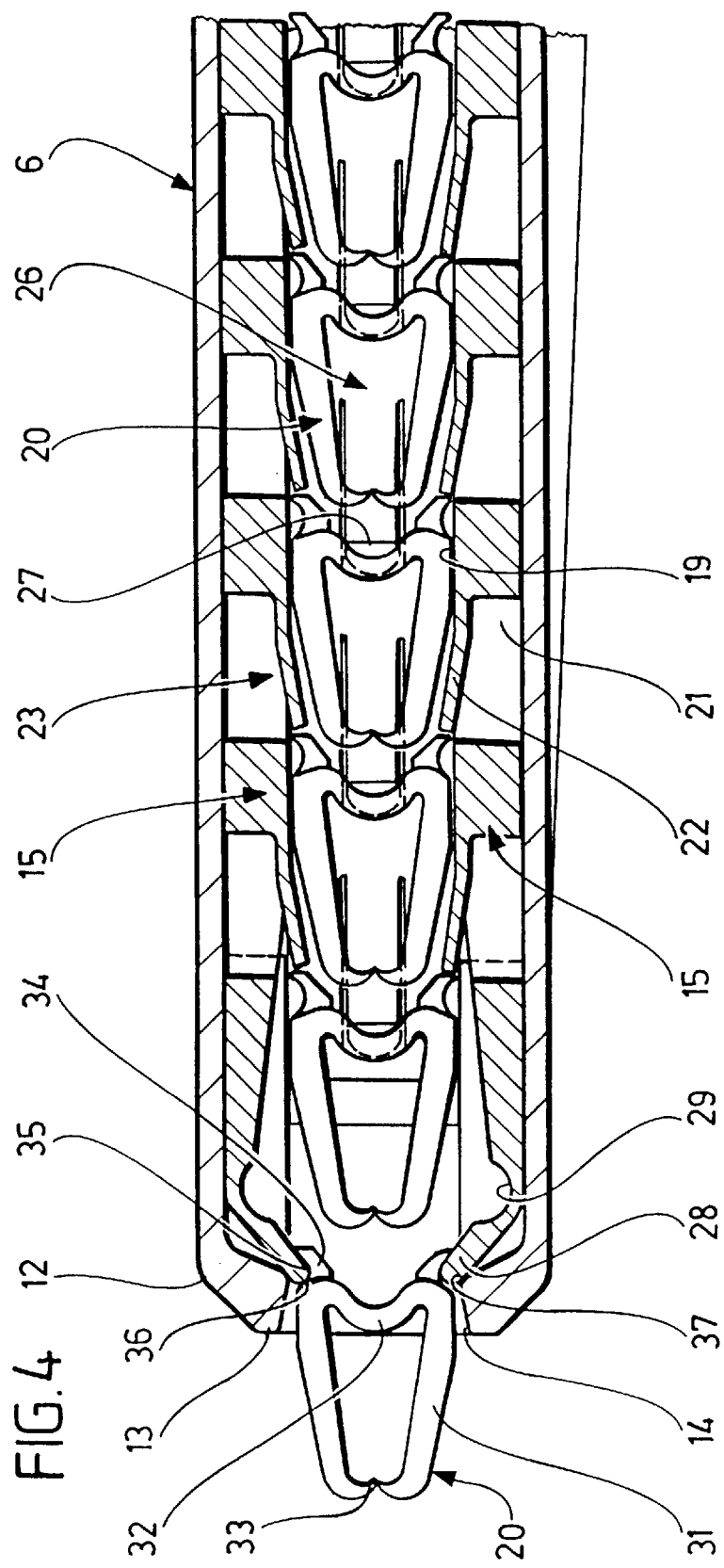

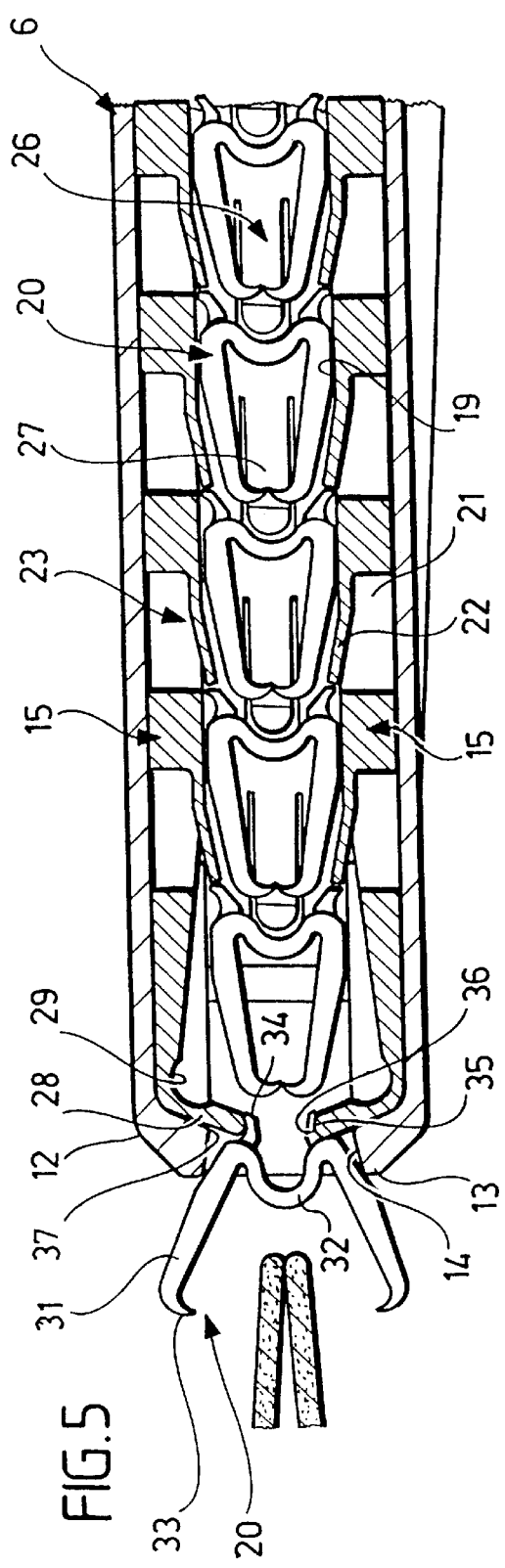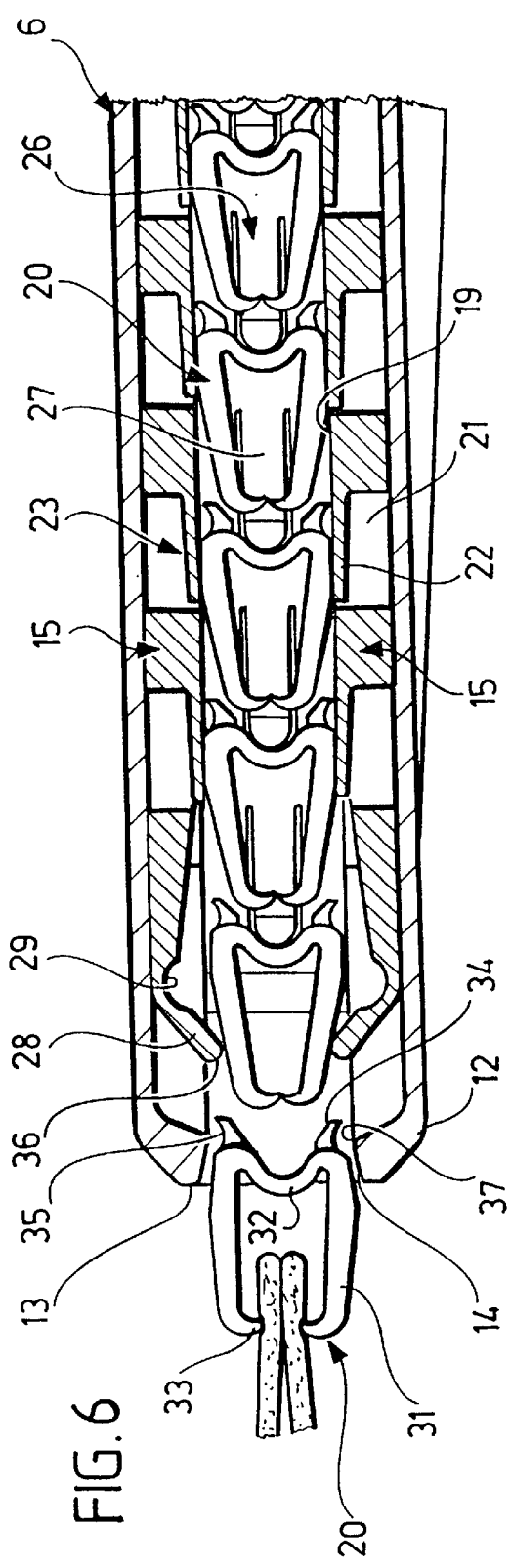

MAGAZINE FOR A SURGICAL CLIP APPLICATOR

This application is a continuation of international application number PCT/EP98/06775 filed Oct. 24, 1998.

BACKGROUND OF THE INVENTION

The invention relates to a magazine for a surgical clip applicator comprising a receiving chamber for clips which are arranged one behind the other and displaceable in the receiving chamber towards its open end, these clips having two arms which are connected via a bridge and pivotable away from one another into an open position contrary to an elastic force and projections which are associated with these arms and project rearwards beyond the bridge, and comprising two opening tools which are located opposite one another, are movable towards one another like pincers and can be abutted on the projections of the respectively foremost clip.

Magazines of this type are used to apply a larger number of clips from them, for example, for clamping the scalp during operations on the head. For this purpose, clip applicators with magazines are already known, in which the clips are stored one behind the other and from which the clips are moved forwards in steps. The respectively foremost clip is grasped by pincer-like opening tools which are movable on clip applicators of this type and mounted stationarily, and these pincer-like opening tools open the clip and apply it at the desired location (DE-PS 37 04 760). With devices of this type the opening tools are part of the devices, only the magazines with the clips accommodated therein can be exchanged.

The object of the invention is to design a generic magazine such that the construction of clip applicators of this type can, altogether, be simplified, in particular, due to the fact that the clip applicators do not require their own mechanism for opening and applying the clips.

BRIEF SUMMARY OF THE INVENTION

This object is accomplished in accordance with the invention, in a magazine of the type described at the outset, in that the opening tools are connected in a hinge-like manner to an advancing element displaceable in the magazine parallel to the direction of displacement of the clips and come to rest on a deflection surface of the magazine during the advancing movement of this advancing element in the direction towards the open end of the receiving chamber and are thereby pivoted inwards transversely to the direction of displacement towards the opening tool located respectively opposite.

With such a solution, the opening tools designed as hinge elements are thus part of the magazine and they are mounted in a simple manner in that they are connected in a hinge-like manner to an advancing element displaceable in longitudinal direction of the magazine. The advancing movement of the advancing elements is utilized to pivot these hinge elements inwards, and this advancing movement is generated by the abutment of the opening tools, which are connected in a hinge-like manner to the advancing elements, on a deflection surface of the magazine. This results in a particularly simple construction not only of the magazine but also of the entire clip applicator since it is sufficient to provide a mechanism on the clip applicator which moves the advancing elements back and forth in the magazine. Special opening tools on the clip applicator itself are no longer necessary.

As a result of this construction, very considerable opening forces can also be generated since the hinge element and the advancing element interact in the manner of a knee joint. The advancing movement is translated into a very slight angular pivoting, in particular, at the end of the advancing movement, and this very slight angular pivoting movement leads to a slight displacement of the opening tool on the clip to be opened, i.e. a reduction in the path of displacement occurs and thus an increase in the corresponding displacement force. The opening forces directed inwards are, for the rest, essentially taken over by the guide means for the advancing element, against which the advancing element abuts and on which the advancing element is thus supported.

It is particularly advantageous when the opening tools are pivotable outwards contrary to an elastic restoring force which is smaller than the force required to open the clips. As a result of this restoring force, the opening tools are pivoted inwards against the clips and abut with their free edges on the clips, in particular, on the projections of the respectively foremost clip but they do not yet open the clip since this elastic restoring force is smaller than the required opening force. This elastic abutment of the opening tools on the foremost clip results in the foremost clip being held between the opening tools until it is moved forwards into the application position.

A particularly advantageous development results when the opening tools are connected to the advancing elements in one piece via a weakened hinge area.

The opening tools and the advancing element can then consist, in particular, of a flexible plastic material so that a cheap construction of the magazine, which can, in this case, also be produced as a disposable part, results.

In accordance with a preferred embodiment it is provided for the deflection surface to be formed by the end wall of the magazine adjoining the open end of the receiving chamber on both sides.

A particularly advantageous construction results when the advancing element has entraining members which can be abutted on the clips for the step-wise advancement of the clips.

The advancing element thus undertakes an additional function, namely that of advancing all the clips which are stored in the magazine and which are moved forwards by the length of a clip with each advancing movement of the advancing element, wherein this advancing movement of the advancing elements also causes the closure of the opening tools at the same time.

In a preferred embodiment it is provided for the opening tools to abut on the projections of the foremost clip during the advancement of the advancing elements before the entraining members of the advancing element abut on following clips. As a result, the respectively foremost clip is moved further forwards than the remaining clips and thus is at a distance from the following clip which is sufficient for the insertion of the opening tools.

The entraining members are designed to be able to disengage from the receiving chamber so that the clips moved forward during the advancement of the advancing element are not drawn back again during the return movement of the advancing elements. The entraining members can thereby be disengaged from the receiving chamber in different ways; in a preferred embodiment it is provided for the entraining members to slide elastically along the clips when the advancing element is withdrawn, i.e., in this case, the clips themselves press the entraining members elastically outwards.

The entraining members can be designed, in particular, as spring tongues which protrude at an angle into the receiving chamber in the direction of advancement. Apart from the entraining function, the spring tongues also have the task with this construction of guiding the clips along their path of displacement and securing them against any tilting.

In a preferred embodiment it is provided for the advancing elements to be designed as half shells which together form the channel-like receiving chamber for the clips.

These half shells are fixed in position relative to one another in the direction of advancement, for example, by means of projections and undercuts interacting in a positive manner so that during the displacement of one advancing element in longitudinal direction the other advancing element is automatically taken along.

In this respect, it is advantageous when the half shells are mounted in an elongated housing of the magazine for displacement in its longitudinal direction.

In this respect, it may be provided for the half shells to be held in mutual abutment by the housing. As a result, a guidance of the half shells by the housing surrounding the half shells is, on the one hand, brought about; on the other hand, it is not necessary to permanently connect the two half shells securely to one another, the abutment by means of the surrounding housing is sufficient to fix the two half shells in position surrounding the clips.

The clips may be secured in position in the receiving chamber against any undesired rearward displacement in various ways, for example, by means of frictional engagement with the side walls.

In accordance with a particularly preferred embodiment, it is provided for retaining projections for the clips, which can be disengaged from the receiving chamber and are fixed in position in longitudinal direction of the magazine, to protrude into the receiving chamber. These are arranged such that the clips can be displaced forwards when the retaining projections are disengaged but are prevented from moving back when the retaining projections are engaged.

The retaining projections may, in particular, be movable flexibly out of the receiving chamber, i.e. the clips press the retaining projections flexibly out of the receiving chamber during advancement but abut on the retaining projections engaged in the receiving chamber during any rearward movement.

It is advantageous when the retaining projections are spring tongues which protrude at an angle into the receiving chamber in the direction of advancement.

In a preferred embodiment, the retaining projections are arranged on the side walls of the receiving chamber. An arrangement then results, with which the entraining members of the advancing elements are, for example, arranged on the upper side and the underside of the clips, the retaining projections, on the other hand, on the two side walls.

It is advantageous when the retaining projections are held on supports which are inserted laterally into the receiving chamber and fixed in position on the magazine so as to be axially non-displaceable. In this respect, these may, for example, be metal strips which have notches bent elastically inwards as retaining projections.

In accordance with a preferred embodiment it is provided for the advancing elements to have on their outer side recesses which adjoin one another in longitudinal direction and in which a transport entrainment means engages which can be displaced back and forth in the direction of displacement of the clips. This transport entrainment means displaces the advancing elements reciprocatingly back and forth in the magazine, wherein, on the one hand, the clips are moved forwards each time by one step while, on the other hand, the respectively foremost clip is opened for application and closed again.

It is favorable when the base of the recess is separated from the advancing element on three sides and forms the entraining member for the clips protruding into the receiving chamber. This results in a particularly simple, constructional design for the advancing elements.

BRIEF DESCRIPTION OF THE SEVERAL VIEWS OF THE DRAWING

The following description of preferred embodiments of the invention serves to explain the invention in greater detail in conjunction with the drawings. These show:

FIG. 2: a sectional view along line 2—2 in FIG. 1;

FIG. 3: a sectional view along line 3—3 in FIG. 2;

FIG. 4: an enlarged partial longitudinal sectional view of the magazine with a clip advanced for application prior to opening;

FIG. 5: a view similar to FIG. 4 with a clip advanced for application and opened and FIG. 6: a view similar to FIG. 4 with the clip applied and the advancing element withdrawn again.

DETAILED DESCRIPTION OF THE INVENTION

Figure 1:
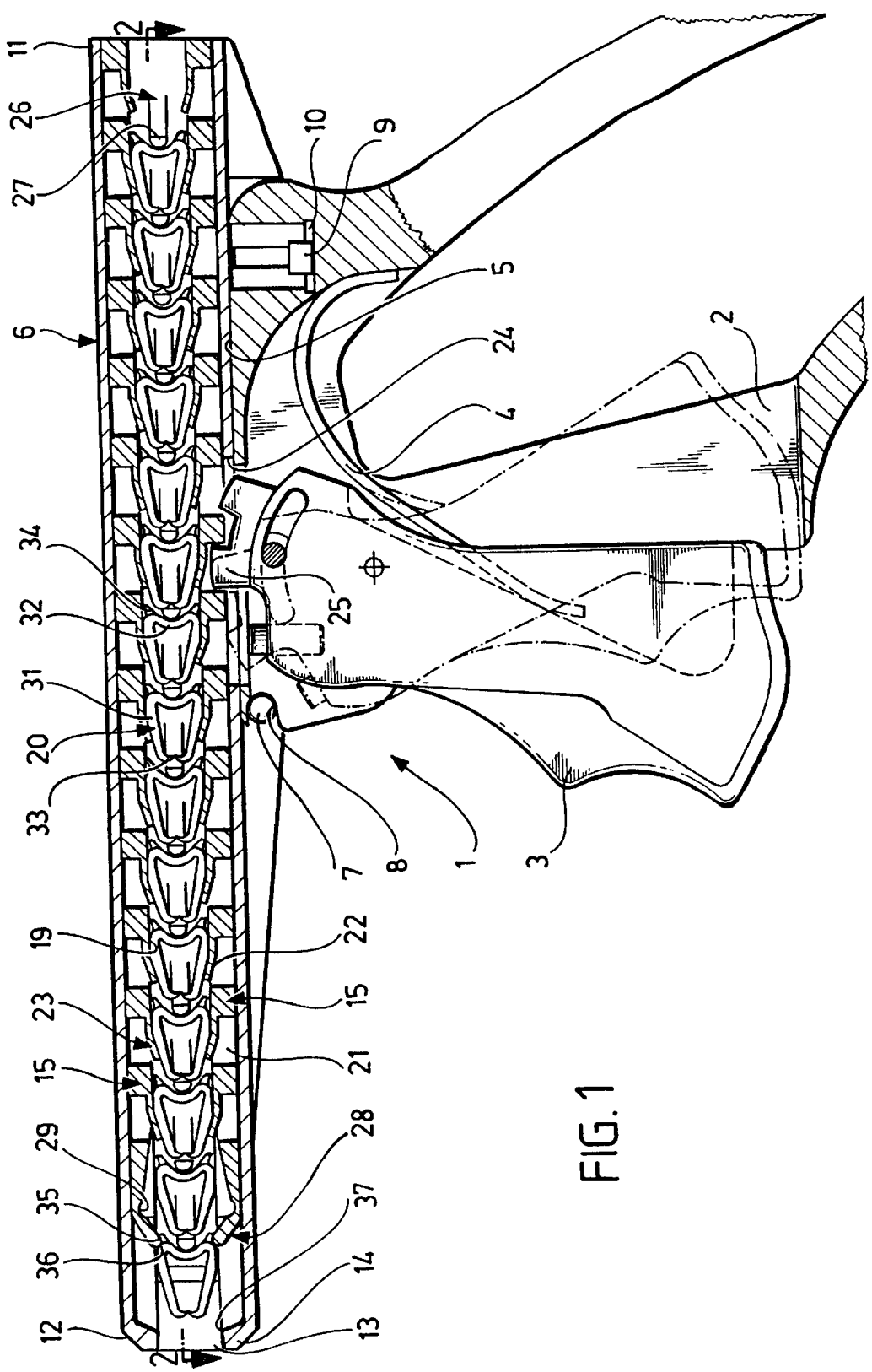
FIG. 1: a longitudinal sectional view of a clip applicator with inserted magazine.

The clip applicator illustrated in the drawings comprises a handpiece 1 with a stationary handle part 2 and an actuating handle 3 which is pivotally mounted thereon and is pivotable into a foremost position by means of a spiral spring 4 secured in position on the handle part 2.

The handpiece 1 terminates towards the upper side with a flat contact surface 5, on which an elongated housing 6 with a rectangular cross section is releasably held. This housing 6 is secured on the contact surface 5 by means of laterally projecting transverse pins 7, which engage in a recess 8 of the handpiece 1 which is open towards the front, and by a locking member 9 which dips into a locking recess 10 of the handle part 2 and can be released by means of suitable actuating means which are not illustrated in the drawings.

The housing 6 is open at its rear end 11; at its front end 12 it is closed by an end wall 13 which has a central outlet opening 14 extending over the entire width of the housing.

Two advancing elements 15 designed as half shells and having the same construction are mounted in the interior of the housing 6 so as to be displaceable longitudinally. These advancing elements 15 abut on one another with their side edges 16 and here engage with projections 17 in recesses 18 of the respectively other advancing element 15 in a positive manner so that the two advancing elements 15 are thereby fixed in position relative to one another in longitudinal direction of the housing 6.

The two advancing elements 15 facing one another with their open side fill the cross section of the housing 6 completely and enclose a receiving chamber 19 which extends over their length and serves to accommodate clips 20 which are U-shaped or C-shaped in cross section.

The two advancing elements 15 have on their upper side and underside, respectively, a number of recesses 21 which are of a parallelepiped design in the embodiment illustrated and are arranged along the center line of the advancing elements 15. The base 22 of each recess 21 is of a relatively thin design and separated on three sides of the recess 21 so that the base 22 is connected to the advancing element 15 only at the rear transverse edge. In addition, the base 22 is deformed inwards so that these bases 22 form tongue-like entraining members 23 which project at an angle inwards and come to rest on the rear side of the clips 20 in a manner explained in more detail further on. The entraining members 23 can be pivoted elastically outwards so that they can be disengaged outwards from the receiving chamber 19 as a result.

An opening 24 is provided in the contact surface 5 of the handpiece 1 and a transport entrainment means 25 which engages in one of the recesses 21 of an advancing element 15 protrudes through this opening. During pivoting of the actuating handle 3, this transport entrainment means 25 is moved forwards relative to the contact surface 5 and thereby takes along the two advancing elements 15. It is thus possible to move the advancing elements forwards by pivoting the actuating handle 3 and move the advancing elements 15 back again by pivoting the actuating handle 3 back. The length of the path of displacement is thereby greater than the length of one clip 20.

In the receiving chamber 19 formed by the two half-shell advancing elements 15, strip-like or plate-like supports 26 are inserted along the side surfaces of the receiving chamber 19 and a row of spring tongues 27, which are directed at an angle into the receiving chamber 19 towards the front end of the housing 6, is separated out of these supports. The supports 26 are fixed in position on the housing 6 by suitable means, e.g., locking elements so as to be non-displaceable in longitudinal direction; the spring tongues 27 thus form retaining elements which protrude into the receiving chamber 19 and can be pivoted flexibly out of it. The distance between adjacent retaining elements is, like the distance between adjacent entraining members on the advancing elements 15, determined by the length of the clips and is slightly greater than this.

At the front end, a wall section 28 is integrally formed on each of the two advancing elements 15 as an extension of the upper side and lower side, respectively, this wall section being connected to the rest of the advancing element in a hinge-like manner by a weakened area 29 such that the wall section 28 is pivotable inwards about a pivot axis extending transversely to the longitudinal direction of the receiving chamber 19. This wall section 28 is pivoted inwards in its rest position and can be pivoted outwards contrary to an elastic restoring force.

The clips 20 filling the receiving chamber 19 one behind the other have two arms 31 which extend essentially parallel to one another and are connected to one another via a bridge 32. They consist of an elastic material, for example, a sterilizable plastic and the two arms 31 are pressed towards one another with their free ends 33 due to the inherent elasticity of the material. These free ends 33 form clamping strips.

In extension of the two arms 31, projections 34 project rearwards beyond the bridge 32 with outwardly directed recesses 35; these projections 34 serve to open the clips. When these projections 34 are brought closer to one another, the bridge 32 bent into the clip in the shape of an arc is deformed and the arms 31 open contrary to the elastic restoring force of the bridge 32.

During use of the clip applicator described, a magazine accommodating the housing 6, the advancing elements 15, the supports 16 and a number of clips 20 inserted into the receiving chamber 19 one behind the other is placed on the contact surface 5 of the handpiece 1 in the manner described. The two advancing elements 15 are thereby located in a withdrawn position, the entraining members 23 designed as flexible locking tongues abut on the respective arms 31 of a clip 20 and thereby align the clip 20 relative to the receiving chamber (FIG. 1).

By actuating the actuating handle 3, the advancing elements 15 are moved forwards, and the entraining members 23 thereby abut with their free edges on the rear sides of the clip 20 located in front of them; as a result, these clips 20 are moved forwards by a clip length together with the advancing element 15. They thereby move the spring tongues 27 of the supports 26 elastically outwards and slide past them.

In their foremost position the clips 20 are advanced to such an extent that the spring tongues 27 can spring back into the receiving chamber again and are positioned with their free edges immediately behind the bridges 32 of the clips 20 moved past them.

When, following this advancing movement of the advancing elements 15, the se are drawn back again, the clips 20 are prevented from moving backwards by the sprung-back spring tongues 27 and are held in their advanced position. During the return movement of the advancing elements 15, the entraining members 23 designed as spring tongues slide along and past the clips 20 held in this manner until they come to rest laterally on the next following clip and position this in the manner described at the outset. All the clips 20 can therefore be displaced forwards by a clip length in the direction towards the outlet opening 14 of the receiving chamber 19 during each actuation of the actuating handle 3.

The respectively foremost clip in the row of clips 20 arranged in the receiving chamber 19 is not moved forwards by an entraining member 23 of the advancing elements 15 but by the wall sections 28 arranged at the front end of the advancing elements 15.

With the advancing elements 15 withdrawn, these wall sections engage with their free edges 36 in the recesses 35 of the projections 34 of the clip 20 and take this clip along during the advancement of the advancing element 15 to such an extent that the clip 20 projects out of the housing 6 with its arms 31 through the outlet opening 14 (FIG. 4). The holding force is thereby applied by means of the elasticity of the wall sections 28 directed inwards; this elastic force is sufficient to hold the clips 20 but not sufficient to open the clips 20.

When the advancing elements 15 are advanced further, the wall sections 28 abut on the edges 37 of the end wall 13 of the housing 6 limiting the outlet opening 14 on both sides and are pivoted inwards even more during the further advancement of the advancing elements 15, i.e. come closer to one another with their free edges 36. The edges 37 of the end wall 13 thus form a deflection surface which pivots the wall sections 28 inwards on account of the advancing movement of the advancing elements 15.

As a result of the movement of the free edges 36 of the wall sections 28, which come closer to one another during this advancing movement of the advancing elements 15, the projections 34 of the clips 20 are also brought closer to one another, and this leads in the manner described to an opening of the arms 31 contrary to the elastic closing force (FIG. 5).

As soon as the clip 20 engages around the desired point of application with the opened arms 31, for example, the location of a cut in the scalp, the clip 20 can be closed again. For this purpose, it is sufficient to move the advancing elements 15 back again by means of the actuating handle 3. The return movement of the advancing elements 15 occurs immediately the actuating handle 3 is pivoted forwards again; the return movement of the advancing element 15 is thereby aided by the spring force of the opened clip which is then closing.

Once the clip 20 has been closed and the advancing elements 15 withdrawn further, the wall sections 28 exit from the recesses 25 of the projections 34 again with their free edge 36 and release the clip 20 which is now in an application position (FIG. 6). During the further movement backwards of the advancing elements 15 the wall sections 28 slide along the following clip which is secured against any displacement backwards by the spring tongues 27 abutting on it. The free edges 36 of the wall sections 28 pass at the end of the return movement into the recesses 35 in the projections 34 of this clip 20 which can then be applied in the desired position during the next advancing cycle in the manner described.

The dimensions are selected such that the entraining members 23 maintain a distance to the clips 20 located in front of them when the advancing element 15 is completely withdrawn while the wall sections 28 already rest with the free edge 36 in the recess 35 of the foremost clip 20. During the advancing movement of the advancing elements 15, only the foremost clip is, first of all, pushed forwards and only then do the entraining members 23 abut on the remaining clips and push these forwards. As a result, the distance between the foremost clip and the following clip is increased so that sufficient space is created for the wall sections 28 which cause the clips to open to dip in.

As soon as the magazine has been emptied in the manner described, it may be removed from the handpiece 1 and replaced by a new, filled magazine.

It is favorable when the advancing elements 15 at least are manufactured in one piece from a flexible, sterilizable plastic material; the housing 6 may also consist of a sterilizable plastic material. The supports 26 with the spring tongues 27 are preferably designed as metal strips.

What is claimed is:

1. A magazine for a surgical clip applicator comprising:
   a receiving chamber for clips arranged one behind the other,
   said clips being displaceable towards an open end of the receiving chamber and having two arms connected via a bridge and being pivotable away from one another into an open position contrary to an elastic force,
   projections associated with said arms and projecting rearwards beyond the bridge,
   said magazine including two opening tools located opposite one another and movable towards one another like pincers and adapted to abut on the projections of the respectively foremost clip, wherein:
   the opening tools are connected in a hinge-like manner to an advancing element displaceable in the magazine parallel to the direction of displacement of the clips, said opening tools being adapted to come to rest on a deflection surface of the magazine during the advancing movement of said advancing element in the direction towards the open end of the receiving chamber, and
   each opening tool is thereby pivoted inwards transversely to the direction of displacement, towards the opening tool located respectively opposite.

2. A magazine as defined in claim 1, wherein the opening tools are pivotable outwards contrary to an elastic restoring force smaller than the force required to open the clips.

3. A magazine as defined in claim 1, wherein the opening tools are connected to the advancing elements in one piece via a weakened hinge area.

4. A magazine as defined in claim 3, wherein the opening tools and the advancing element consist of a flexible plastic material.

5. A magazine as defined in claim 3, wherein the deflection surface is formed by the end wall of the magazine adjoining the open end of the receiving chamber on both sides.

6. A magazine as defined in claim 1, wherein the deflection surface is formed by the end wall of the magazine adjoining the open end of the receiving chamber on both sides.

7. A magazine as defined in claim 1, wherein the advancing element has entraining members adapted to abut on the clips for the step-wise displacement of the clips.

8. A magazine as defined in claim 7, wherein the opening tools abut on the projections of the foremost clip during the advancement of the advancing element before the entraining members of the advancing element (15) abut on the following clips.

9. A magazine as defined in claim 8, wherein the entraining members slide elastically along the clips when the advancing element is withdrawn.

10. A magazine as defined in claim 9, wherein the entraining members are designed as spring tongues protruding at an angle into the receiving chamber in the direction of advancement.

11. A magazine as defined in claim 1, wherein the advancing elements are designed as half shells together forming the channel-like receiving chamber for the clips.

12. A magazine as defined in claim 11, wherein the half shells are fixed in position relative to one another in the direction of advancement.

13. A magazine as defined in claim 11, wherein the half shells are mounted in an elongated housing of the magazine for displacement in its longitudinal direction.

14. A magazine as defined in claim 13, wherein the half shells are held in mutual abutment by the housing.

15. A magazine as defined in claim 1, wherein retaining projections for the clips protrude into the receiving chamber, said retaining projections being disengageable from said receiving chamber and fixed in position in the longitudinal direction of the magazine.

16. A magazine as defined in claim 15, wherein the retaining projections are movable flexibly out of the receiving chamber.

17. A magazine as defined in claim 16, wherein the retaining projections are spring tongues protruding at an angle into the receiving chamber in the direction of advancement.

18. A magazine as defined in claim 15, wherein the retaining projections are arranged on the side walls of the receiving chamber.

19. A magazine as defined in claim 18, wherein the retaining projections are held on supports inserted laterally into the receiving chamber and fixed in position on the magazine so as to be axially non-displaceable.

20. A magazine as defined in claim 1, wherein the advancing elements have, on their outer side recesses adjoining one another in a longitudinal direction, a transport entrainment means displaceable back and forth in the direction of displacement of the clips engaging in said recesses.

21. A magazine as defined in claim 20, wherein the base of the recess is separated from the advancing element on three sides and forms the entraining member for the clips protruding into the receiving chamber.

* * * * *